United States Patent
Yang (10) Patent No.: US 10,251,786 B2
(45) Date of Patent: Apr. 9, 2019

(54) METHOD AND APPARATUS FOR CONTROLLING OPENING OF AN AUTO-DARKENING FILTER IN AN EYE PROTECTION DEVICE

(71) Applicant: OPTREL HOLDING AG, Appenzell (CH)

(72) Inventor: Sheng Yang, Wattwil (CH)

(73) Assignee: OPTREL HOLDING AG, Appenzell (CH)

( * ) Notice: Subject to any disclaimer, the term of this patent is extended or adjusted under 35 U.S.C. 154(b) by 978 days.

(21) Appl. No.: 14/086,587

(22) Filed: Nov. 21, 2013

(65) Prior Publication Data

US 2015/0135389 A1    May 21, 2015

(51) Int. Cl.
*A61F 9/06*    (2006.01)

(52) U.S. Cl.
CPC ............. *A61F 9/067* (2013.01); *A61F 9/06* (2013.01); *A61F 9/065* (2013.01)

(58) Field of Classification Search
CPC ............ A61F 9/067; A61F 9/06; A61F 9/065
USPC ............................................................. 2/8.2
See application file for complete search history.

(56) References Cited

U.S. PATENT DOCUMENTS

| | | | |
|---|---|---|---|
| 4,237,557 A | 12/1980 | Gordon | |
| 4,241,286 A | 12/1980 | Gordon | |
| 4,620,322 A | 11/1986 | Eggenschwiler et al. | |
| 4,863,244 A | 9/1989 | Fuerthbauer et al. | |
| 4,920,257 A | 4/1990 | Fuerthbauer et al. | |
| 5,248,880 A | 9/1993 | Fergason | |
| 5,444,232 A | 8/1995 | Gunz et al. | |
| 6,067,129 A | 5/2000 | Fergason | |
| 6,070,264 A | 6/2000 | Hamilton et al. | |
| 6,483,090 B1 | 11/2002 | Bae | |
| 6,841,772 B1 | 1/2005 | Hamilton | |
| 6,881,939 B1 | 4/2005 | Hamilton et al. | |
| 7,026,593 B2 | 4/2006 | Hamilton | |
| 7,161,116 B2 | 1/2007 | Steinemann | |
| 7,161,135 B2 | 1/2007 | Fergason | |
| 7,358,472 B2 | 4/2008 | Hamilton | |

(Continued)

FOREIGN PATENT DOCUMENTS

| | | |
|---|---|---|
| WO | 2009/045676 A1 | 4/2009 |
| WO | 2013/166231 A1 | 11/2013 |

OTHER PUBLICATIONS

Feb. 24, 2015 extended European Search Report issued in Application No. 14194084.1.

(Continued)

*Primary Examiner* — Alissa L Hoey
(74) *Attorney, Agent, or Firm* — Oliff PLC (57) ABSTRACT

An eye protection device for a welding mask or the like includes a welding activity detection circuit that is configured to detect welding activity, and a filter driver that controls an optical filter to be in undarkened and darkened states. The filter driver is configured to (i) provide a slower and/or gradual opening of the filter, (ii) insert a user-selected delay and/or gradient between the end of welding activity and the opening of the filter, and/or (iii) cause variation of light transmission values of the filter between a darkened state and an undarkened state based on varying brightness detected by a brightness sensor during transition of the filter from a darkened state to an undarkened state.

5 Claims, 12 Drawing Sheets

(56) References Cited

U.S. PATENT DOCUMENTS

| | | | |
|---|---|---|---|
| 8,049,151 B2* | 11/2011 | Huh | A61F 9/06 2/8.2 |
| 8,119,974 B2 | 2/2012 | Hamilton et al. | |
| 8,181,270 B2 | 5/2012 | Steinemann | |
| 8,955,162 B2* | 2/2015 | Huh | A61F 9/067 2/8.2 |
| 8,959,662 B2* | 2/2015 | Huh | A61F 9/067 2/8.2 |
| RE45,677 E* | 9/2015 | Steinemann | A61F 9/065 |
| 2005/0001155 A1 | 1/2005 | Fergason | |
| 2005/0133685 A1 | 6/2005 | Hamilton | |
| 2006/0285330 A1* | 12/2006 | Sundell | A61F 9/067 362/293 |
| 2007/0056072 A1 | 3/2007 | Steinemann | |
| 2007/0131845 A1* | 6/2007 | Huh | A61F 9/067 250/206.1 |
| 2008/0158502 A1* | 7/2008 | Becker | A61F 9/067 351/44 |
| 2009/0094721 A1* | 4/2009 | Becker | A61F 9/067 2/8.8 |
| 2010/0090997 A1* | 4/2010 | Huh | A61F 9/067 345/207 |
| 2010/0132086 A1* | 6/2010 | Huh | A61F 9/067 2/8.2 |
| 2010/0287676 A1* | 11/2010 | Seo | A61F 9/064 2/8.2 |
| 2011/0083241 A1* | 4/2011 | Cole | A61F 9/06 2/8.2 |
| 2011/0159918 A1* | 6/2011 | Huh | A61F 9/067 455/556.1 |
| 2012/0081162 A1* | 4/2012 | Greiner | A61F 9/067 327/171 |
| 2012/0176659 A1* | 7/2012 | Hsieh | A61F 9/067 359/272 |
| 2012/0204303 A1* | 8/2012 | Seo | A61F 9/023 2/12 |
| 2012/0291172 A1* | 11/2012 | Wills | B23K 9/0956 2/8.2 |
| 2013/0026150 A1* | 1/2013 | Chantry | A61F 9/067 219/136 |
| 2013/0097760 A1* | 4/2013 | Feinberg | G02B 7/006 2/8.2 |
| 2013/0291271 A1* | 11/2013 | Becker | G06F 3/005 2/8.2 |
| 2014/0020147 A1* | 1/2014 | Anderson | A61F 9/06 2/8.2 |
| 2014/0320771 A1* | 10/2014 | Keller | A61F 9/067 349/14 |
| 2015/0067941 A1* | 3/2015 | Huh | A61F 9/067 2/8.2 |
| 2015/0320601 A1* | 11/2015 | Gregg | G06T 7/10 345/8 |
| 2016/0125653 A1* | 5/2016 | Denis | B23K 9/322 348/90 |
| 2016/0346131 A1* | 12/2016 | Fergason | A61F 9/065 |

OTHER PUBLICATIONS

Oct. 2, 2014 Office Action issued in U.S. Appl. No. 14/088,100.
Jun. 22, 2018 Office Action issued in European Patent Application No. 14 194 084.1-1122.

* cited by examiner

METHOD AND APPARATUS FOR CONTROLLING OPENING OF AN AUTO-DARKENING FILTER IN AN EYE PROTECTION DEVICE

BACKGROUND

This invention relates to an eye protection device that can be used, for example, in a welding protective mask.

Figure 1:
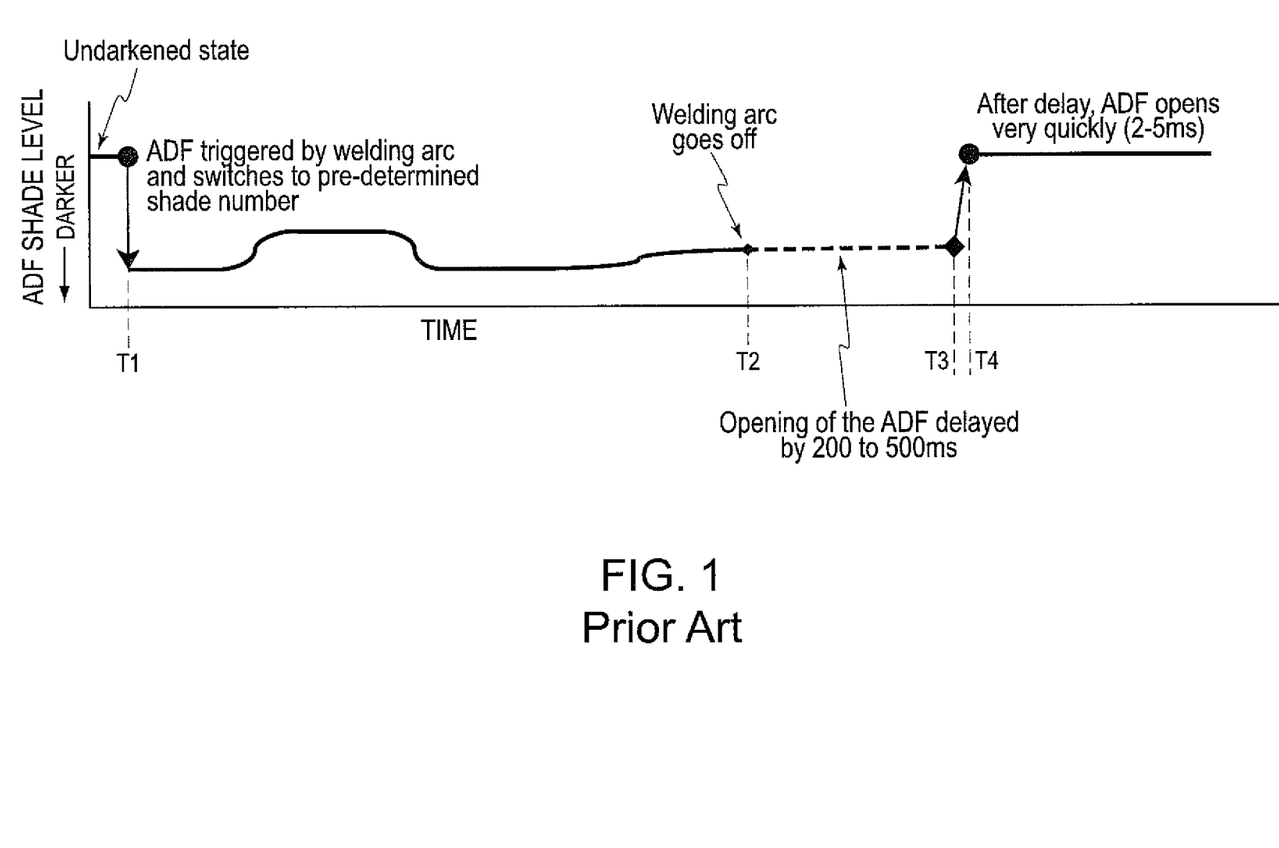
FIG. 1 is a chart showing an ADF shade level over time in a conventional eye protection device.

Eye protection devices are known in which an auto-darkening filter (ADF), typically comprising a liquid crystal cell, is driven from an undarkened state to a darkened state that protects a user's eyes from a welding flash or the like. FIG. 1 shows a timing chart of such an operation in a conventional eye protection device. The ADF starts in an undarkened state, and then is driven to a darkened state at time T1, upon detection of welding activity. A darkened state (either constant or varied) is maintained until time T2, at which welding activity is no longer detected (e.g., when an electric welding arc goes off). Thereafter, after a predetermined delay of from about 200 to about 500 milliseconds, the ADF returns very quickly to the undarkened state over the period of T3 to T4, a time of from about 2 milliseconds to about 5 milliseconds.

SUMMARY

With such a quick return to the undarkened state, there is a risk that a welder's eyes may be exposed to bright light while the pupils are dilated, even though the welding activity has ended. For example, in electric arc welding operations on relatively thick metal, involving relatively high amperage, such as 300 amps or more, the weld may continue to glow brightly for up to several minutes (and very harsh brightness levels may last for at least several seconds).

To help reduce this risk, embodiments of this invention (i) provide a slower and/or gradual opening of the ADF, (ii) insert a user-selected delay and/or gradient between the end of welding activity and the opening of the ADF, and/or (iii) cause variation of light transmission values of the optical filter between a darkened state and an undarkened state based on varying brightness detected by a brightness sensor during transition of the ADF from a darkened state to an undarkened state.

BRIEF DESCRIPTION OF THE DRAWINGS

Exemplary embodiments will be described with reference to the accompanying drawings, in which like numerals represent like parts, and wherein.

DETAILED DESCRIPTION OF EMBODIMENTS

As described in more detail below, in embodiments, the invention may perform, separately or in any combination, (i) controlling a transition period from (a) a beginning of transition of the optical filter from the darkened state to the undarkened state to (b) an end of transition of the optical filter from the darkened state to the undarkened state to include a user-selected gradient; (ii) inserting a user-selected delay between (a) an end of welding activity detection and (b) the beginning of transition of the optical filter from the darkened state to the undarkened state; (iii) cause variation of light transmission values of the optical filter between the darkened state and the undarkened state based on varying brightness detected by a brightness sensor during the transition period; or (iv) controlling the transition period to be at least 10 milliseconds.

These features, separately or in any combination, may allow a user-selected and/or preset gradual transition of the optical filter from the darkened state to the undarkened state, and/or a delay of user-selected length before the transition begins. A gradual transition may be safer and/or more comfortable for a user, and helps avoid damage and/or strain to the user's eyes that may be caused by rapid pupil contraction. A user-selected length of delay allows a user to, for example, adjust an eye protection device to respond differently for different welding tasks or the like, according to expected or previously-experienced brightness levels after a welding activity or the like ends.

The gradual transition may be the result of either or both of (a) one or more user-selected and/or preset (e.g., factory-set) gradients in the transition period and (b) variation of light transmission values of the optical filter between the darkened state and the undarkened state based on varying brightness detected by a brightness sensor during the transition period. The transition period may in embodiments be longer than conventional transitions periods, and may, for example, be at least 10 milliseconds. The transition period may be long enough to be perceived by the human eye, rather than being perceived as an instantaneous change. The transition period may be up to several (e.g., 2, 3, 5, 10, 15, 20, 30, 45) seconds, or up to a minute or more. A relatively long transition period is particularly beneficial in cases of welding at relatively high amperage, such as 300 amps or more, and/or on relatively thick metal, such as metal having a thickness of one inch, two inches, three inches or more. In some embodiments, the user may have the option of selecting a gradient that results in as short a transition period as possible, such as from about 1 millisecond to about 5 milliseconds. This option may allow a user to set a welding mask differently for different types of welding and/or for different types of welding tasks.

Figure 2:
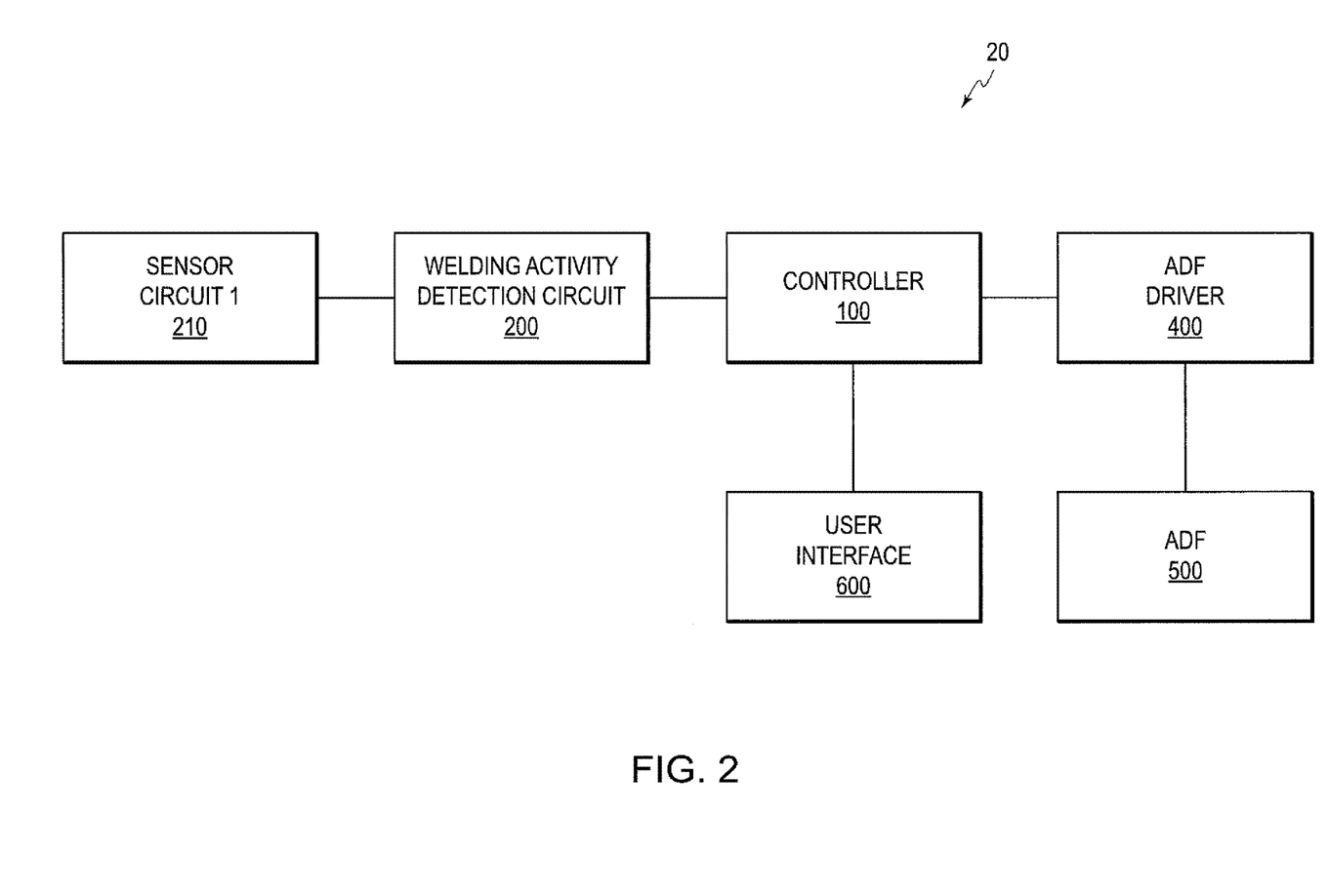
FIG. 2 is a functional block diagram illustrating an exemplary embodiment of an eye protection device.

FIG. 2 is a function block diagram of an eye protection device 20. The eye protection device 20 includes a controller 100, a welding activity detection circuit 200 connected to the controller 100, a sensor circuit 210 connected to the welding activity detection circuit 200, an ADF driver 400 connected to the controller, an auto-darkening filter (ADF) 500 connected to the ADF driver 400, and a user interface 600 connected to the controller 100. One or more power sources (not depicted), such as a battery and/or solar cell, may provide electrical power to the controller 100 and/or the ADF driver 400.

The controller 100 may be either a digital controller, such as a programmed microcontroller with one or more software programs stored in a memory, or an analog controller, in which inputs, switches and outputs are arranged, in a known manner, to convert inputs from the welding activity detection circuit 200, and optionally from one or more other circuits such as the transmission control circuit 300 described below in connection with FIG. 3, into drive signals. The output from the controller 100 is input to the ADF driver 400.

The welding activity detection circuit 200 detects welding activity in any known way, such as by (i) detecting a welding flash through an optical sensor that is part of the sensor circuit 210, (ii) detecting, through a magnetic field sensor that is part of the sensor circuit 210, a change in the magnetic field emitted by a welding apparatus, or (iii) detecting an electrical current change through electrical welding leads as welding activity commences, through a current sensor that is part of the sensor circuit 210.

The sensor circuit 210 may include or be connected to one or more sensors. In one or more embodiments, the sensor circuit 210 may include only a single sensor. In one or more other embodiments, the sensor circuit 210 may include a plurality of sensors, which may all be of the same type or which may include sensors of different types. One or more of the sensors may be optical sensors. As is known by those skilled in art, a solar cell can serve as both an optical sensor and a power source. The connection between the sensor circuit 210 and the welding activity detection circuit 200, and/or the connection between the sensor circuit 210 and one or more of the sensors, may be a wired connection, or a wireless connection using known wireless technology such as BLUETOOTH or the like. One or more of the sensors may be located on a welding mask or the like, such as described below in connection with FIG. 12. Alternatively, one or more of the sensors may be located remotely from the eye protection device 20, such as on, near or incorporated within a welding electrode holder or wire-feed handpiece, or on, near or incorporated within a welding machine to which welding leads are connected. A remotely located sensor may, for example, communicate with the sensor circuit 210 or the welding activity detection circuit 200 wirelessly by sending signals to a wireless receiver unit that is part of or operatively connected to the sensor circuit 210 or the welding activity detection circuit 200.

The sensor circuit 210, the welding activity detection circuit 200 or the controller 100 may include a flicker detection circuit that distinguishes the typical welding flicker from ambient light fluctuations, and/or a threshold circuit that, for example, causes the ADF to be in a darkened state only when a predetermined threshold of light brightness, magnetic field intensity, or electrical current change is reached or exceeded. One or more noise filters may also be included at one or more appropriate points along the path from the sensor circuit 210 to the controller 100. Examples of such flicker detection circuits, threshold circuits and noise filters, and their appropriate placement within an eye protection device, are known to those skilled in the art.

The ADF driver 400 may serve as a power stage, and causes the ADF 500 to be in an undarkened state or a darkened state, as described in detail below.

The ADF 500 is an optical filter that may, for example, include a known liquid crystal cell that can be driven to an undarkened state and one or more darkened states. The undarkened state is not necessarily a completely transparent state, and refers to the lightest state, i.e., the state of greatest visible light transmission, of the ADF 500. The European Standard EN 379 regulates the use of automatic welder protecting filters in Europe. European Norm EN 169 defines various shade levels ("Shade Numbers"), which are light transmission values, and EN 379 regulates the Shade Number as a function of illuminance. The European Standard EN 379 and European Norm EN 169 are incorporated herein by reference in their entireties. Shade Numbers are similarly defined in the corresponding U.S. standard. The undarkened state of an ADF typically is in a range of about Shade Number 3 to about Shade Number 5, as defined in the European standard. The most opaque darkened state of an ADF is typically about Shade Number 14, as defined in the European standard.

As is known in the art, to achieve a desired maximum shade level, two or more liquid crystal cells, possibly connected to separate drivers, may be placed in series to achieve darker shade levels. Thus, while FIG. 2 depicts a single ADF driver and a single ADF, there may in fact be multiple ADF's and/or multiple ADF drivers in the eye protection device 20. As is also known in the art, one or more passive filters to protect against harmful wavelengths of radiation, such infrared or ultraviolet wavelengths, can also be included along with the ADF in the form of a coating, pigment or the like.

The user interface 600 may be any known or later-developed interface configured to allow a user to input one or more desired operating values, function selections, mode selections or the like to the controller 100. For example, as described in more detail below, a user may select a desired length and/or gradient of a transition period during which the ADF 500 changes from a darkened state to the undarkened state. As another example, a user may select whether a delay is inserted between the end of welding activity detection (e.g., the point at which welding stops) and the beginning of the transition period, and/or the length of such delay. As another example, the user interface may be configured to allow a user to select either a welding mode, in which the ADF 500 automatically darkens in response to detection of bright light, or a grind mode (known to those skilled in the art), in which the ADF 500 remains in the undarkened state even in the presence of bright sparks from a grinder. (The grind mode allows the eye protection device to be used as both a welding protection mask and a grinding protection shield, so that a user need not switch eye and face protection gear between welding and grinding operations.) As another example, the user interface 600 may be configured to allow a user to select a desired shade level for a darkened state of the ADF 500.

The user interface 600 may include one or more micro-switches or other switches, one or more soft switches on an LCD display or the like, one or more knobs, or the like, or any combination of switches, knobs and the like. The connections between the switches and/or knobs and the controller 100 may be wired or wireless, and in embodiments, the switches and/or knobs can be located at an inner surface of a welding mask, an outer surface of the welding mask, and/or at a location remote from the welding mask, in any desired combination.

Figure 3:
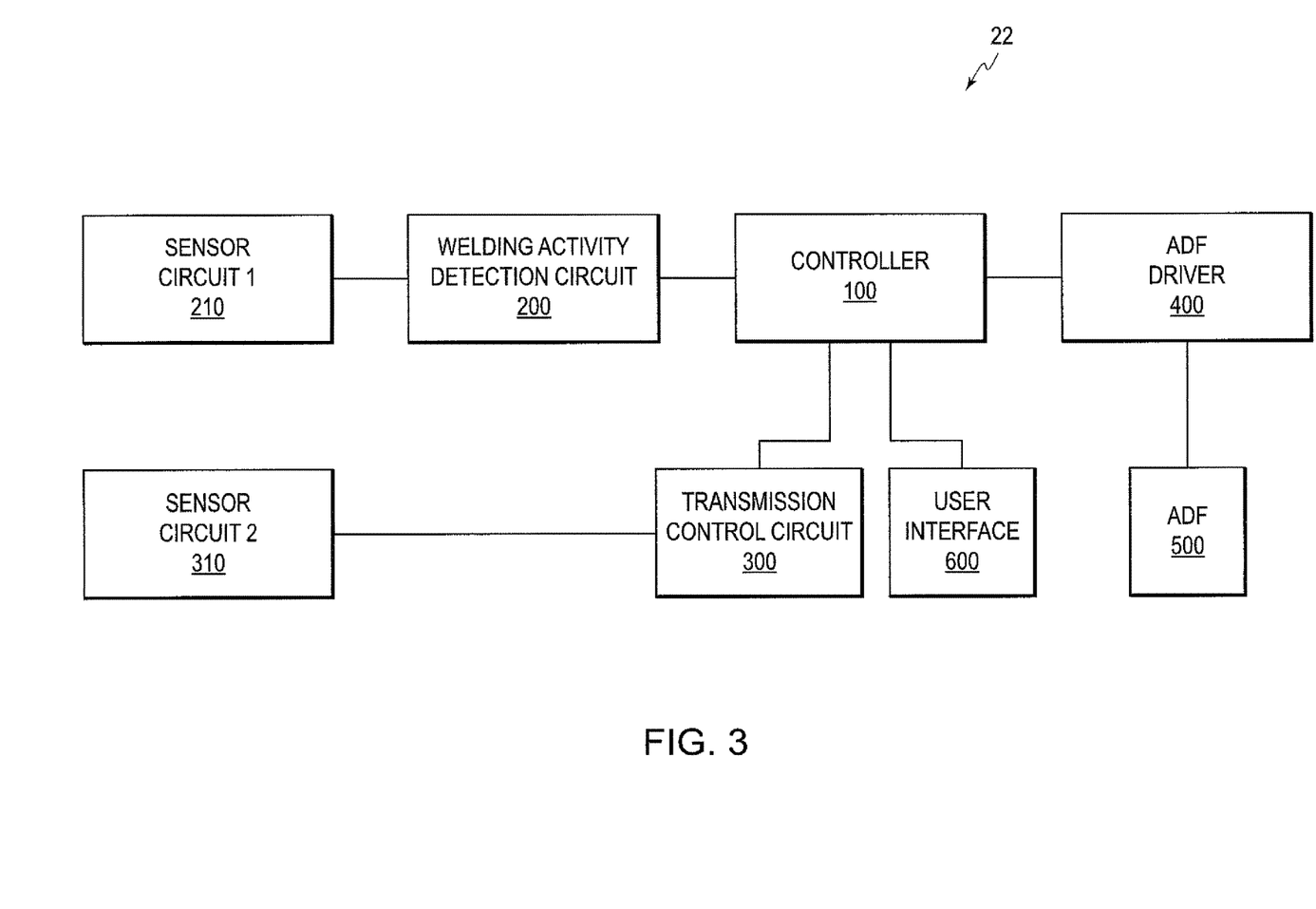
FIG. 3 is a functional block diagram illustrating an exemplary embodiment of an eye protection device.

FIG. 3 is a function block diagram of an eye protection device 22. The eye protection device 22 is similar to the eye protection device 20 of FIG. 2, except that the eye protection device 22 includes a transmission control circuit 300 operably connected to the controller 100, and a sensor circuit 310 connected to the transmission control circuit 300. The sensor circuit 310 may include or be connected to one or more brightness sensors that detect brightness of a welding flash during welding, and that may also or alternatively detect brightness of a weld after welding activity has ended.

Based on outputs from the sensor transmission control circuit 300 and the sensor circuit 310, the controller 100 causes the ADF driver 400 to drive the ADF 500 to a shade level based on a perceived brightness level. Specifically, the sensor circuit 310 outputs a signal that is based on a perceived brightness level detected by a brightness sensor, and the transmission control circuit 300 outputs a transmission control signal to the ADF driver 400 based on the perceived brightness level.

The light transmission value (shade level) of the ADF in the darkened state (i.e., during welding activity) may be based on the transmission control signal. With this structure, the eye protection device 22 may have both a manual mode, in which a user selects a desired shade level to which the ADF driver 400 drives the ADF 500 during welding, or an automatic mode, in which the shade level changes during welding in response to detected brightness variations detected by the brightness sensor. Such a manual mode and automatic mode are disclosed in U.S. Pat. No. 8,181,270, the disclosure of which is incorporated herein by reference in its entirety. Alternatively, the eye protection device 22 may have only an automatic mode (optionally with manual fine tuning adjustment, such as is disclosed in the 270 patent).

Additionally or alternatively, transmission values of the optical filter during a transition period from a darkened state to the undarkened state may be based on the transmission control signal. With this structure, the brightness of the weld may continue to be detected after welding activity has stopped, and the ADF 500 may be gradually driven through various shade levels during the transition period so that the welder can continue to observe the weld as it changes from a hot, bright state to a cooler, less-bright state.

Additionally, in the eye protection device 22, the user interface 600 may be configured to allow the user to select from among the various additional options discussed above in connection with FIG. 3.

In FIG. 3, separate sensors are shown for the welding activity detection circuit 200 and the transmission control circuit 300, but in embodiments the same sensor, or same group of sensors, may provide sensor input to both the welding activity detection circuit 200 and the transmission control circuit 300. Additionally, as discussed above in connection with the sensor circuit 210 and the welding activity detection circuit 200, the connection between the sensor circuit 310 and the transmission control circuit 300, and/or the connection between the sensor circuit 310 and one or more of the sensors, may be wired or wireless, and one or more of the sensors may be located remotely from the eye protection device 22.

Figure 4:
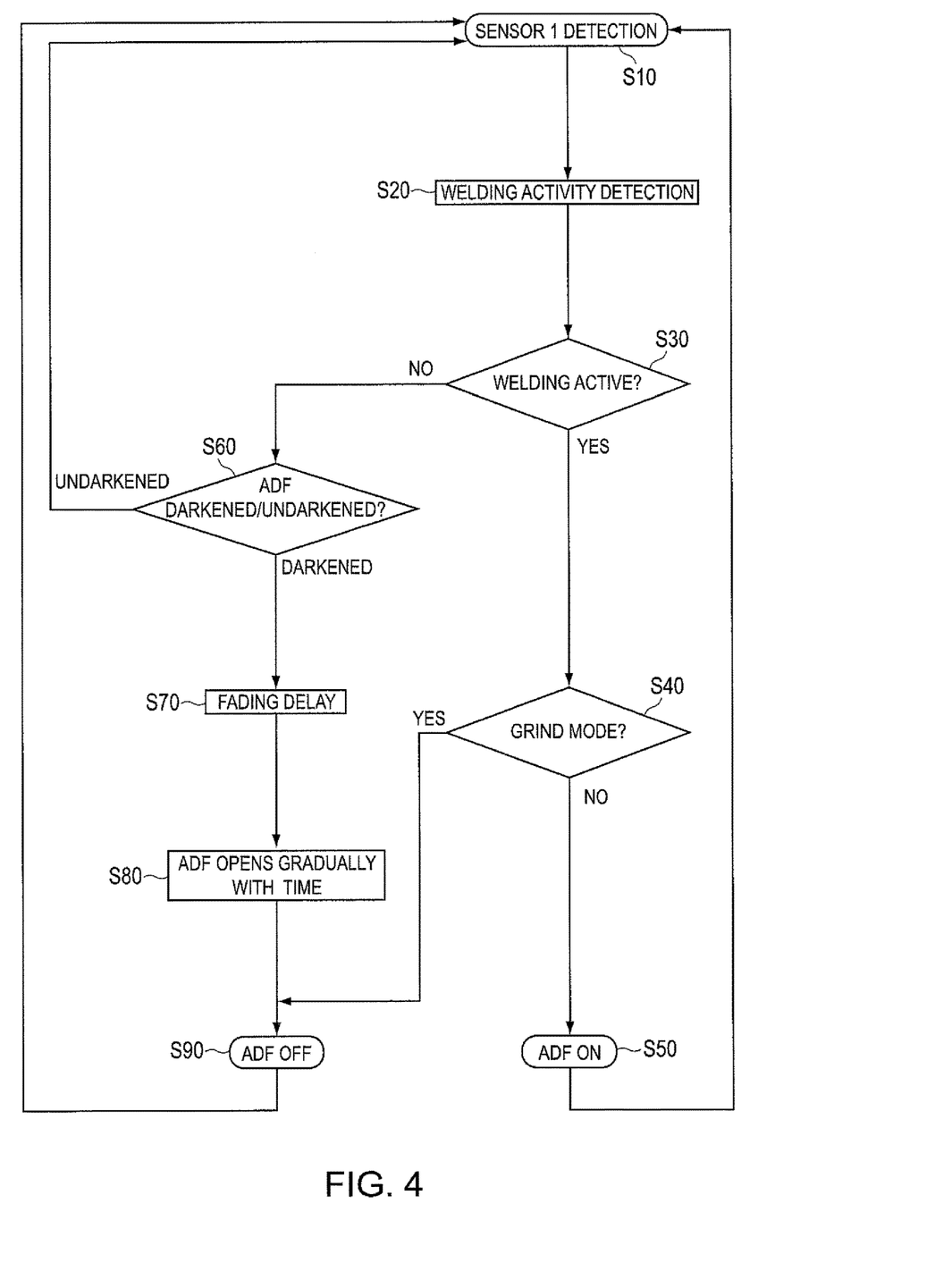
FIG. 4 is a flowchart illustrating an exemplary eye protection method.

FIG. 4 is a flowchart illustrating a first exemplary eye protection method that may be performed by, for example, the eye protection device 20 of FIG. 2 or the eye protection device 22 of FIG. 3.

Beginning in step S10, a sensor detects welding light, a magnetic field change, a current change, or the like, and outputs a sensor signal. In step S20, welding activity detection is performed based on the sensor signal output in step S10. The method then continues to step S30.

In step S30, a determination is made as to whether welding is active, e.g., whether an electric welding arc is present between a welding electrode and a workpiece. This determination may be made by using, for example, one or more sensors and a welding activity detection circuit such as those described above. If welding is active, the method continues to step S40. Otherwise, the method proceeds to step S60.

Step S40 is an optional step that may be included if the eye protection device has a grind mode or other mode(s) (hereafter grind mode). If step S40 is not included, the method proceeds directly to step S50 from S30 upon a "YES" determination. In step S40, it is determined whether the eye protection device is set to a grind mode. If the grind mode is not set, the method continues to step S50, causes an ADF to switch to or remain in an ON state (darkened state), and returns to step S10. If the grind mode is set, the method proceeds to step S90, the ADF is in an OFF state (undarkened state), and the method returns to step S10.

In step S60, upon determination in step S30 that welding is not active, a determination is made as to whether the ADF is in an undarkened state (OFF) or a darkened state (ON). If the ADF is in an undarkened state, the method returns to step S10. If the ADF is in a darkened state, the method may continue to optional step S70, where a fading delay is performed. The fading delay is a delay between the detection of the end of welding activity and the beginning of a transition of the ADF from a darkened state to the undarkened state, and as discussed below in connection with FIGS. 8 and 9, for example, may be either a user-selected delay set through a user interface of the eye protection device, or a factory-set delay.

After the fading delay is performed in step S70, the method continues to optional step S80, in which the ADF opens gradually with time. The gradual opening can, for example, be a result of controlling a transition period from (a) a beginning of transition of the ADF from the darkened state to the undarkened state to (b) an end of transition of the ADF from the darkened state to the undarkened state to include a user-selected gradient or pre-set gradient.

Either or both of steps S70 and S80 can be included in the method of FIG. 4, as will be appreciated from the following description of FIGS. 6-11.

After completion of optional step S70 and/or step S80, the method proceeds to step S90, the ADF is in an OFF state (undarkened state), and the method returns to step S10.

Figure 5:
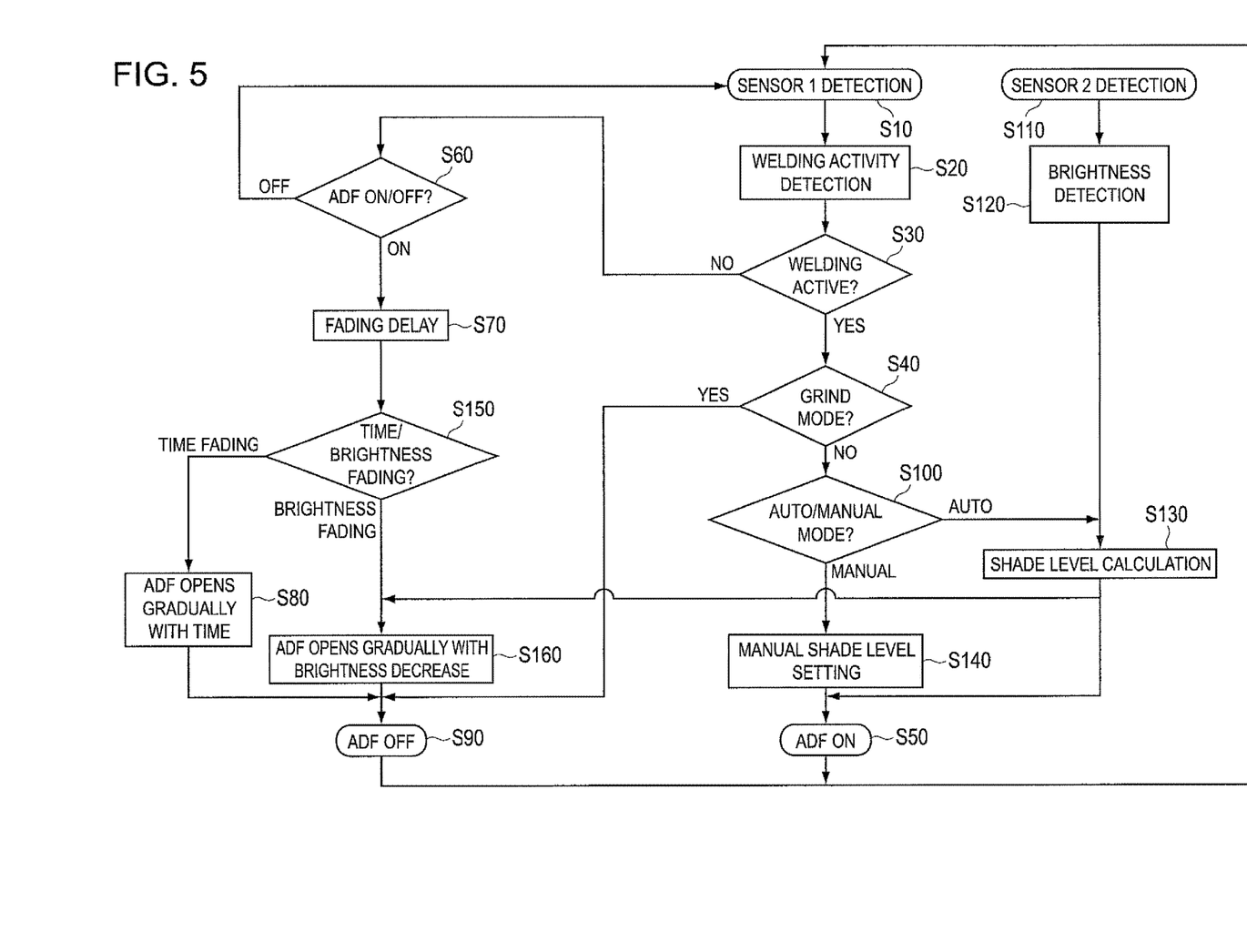
FIG. 5 is a flowchart illustrating an exemplary eye protection method.

FIG. 5 is a flowchart illustrating a second exemplary eye protection method that may be performed by, for example, the eye protection device 22. The description of steps corresponding to those in FIG. 4 will be omitted. As in FIG. 4, step S40 of FIG. 5 is an optional step, as are steps S70 and S80. Steps S100, S140, S150 and S160 are also optional, as described in detail below.

In step S100, a determination is made as to whether the eye protection device is in a manual mode, in which a user has manually set a desired shade level for a darkened state of the ADF, or an automatic mode, in which an appropriate shade level is automatically determined based on detected brightness of the welding activity. As discussed above, such a manual mode and automatic mode are disclosed in U.S. Pat. No. 8,181,270. If the eye protection device is set to a manual mode, the method proceeds to step S140. Otherwise, the method proceeds to step S130. If the eye protection device has only a manual mode or only an automatic mode, then steps S100 and S140 are omitted and the method proceeds to step S50.

Separately, in step S110, a sensor (which may be a different sensor than the sensor used for step S10, or, if it is an optical sensor, the same sensor used for step S10) detects light from a welding flash (such as an electric welding arc), and/or detects light from a weld after welding activity has ended, and outputs a sensor signal. In step S120, brightness detection is performed based on the sensor signal output in step S110.

In step S130, a shade level calculation is performed based on the result of the brightness detection of step S120. The result of this determination is used in step S160, described below, and is also used in step S50, if the eye protection device has an automatic mode and is set to the automatic mode.

In step S140, upon determination that the eye protection device is in a manual mode, the method performs shade level setting based on the shade level manually selected by a user. The method then proceeds to step S50.

In step S50, the method causes an ADF to switch to or remain in an ON state (darkened state), based on the shade level set in step S140, or based on the shade level calculation of step S130. The method then returns to step S10.

In step S60, upon determination in step S30 that welding is not active, a determination is made as to whether the ADF is in an undarkened state (OFF) or a darkened state (ON). If the ADF is OFF, the method returns to step S10. If the ADF is ON, the method may, as in the method of FIG. 4, continue to optional step S70, where a fading delay is performed.

After the fading delay is performed in step S70, if the eye protection device is provided with both a time fading mode and a brightness fading mode, the method proceeds to step S150 and performs a determination as to whether the device is set to the time fading mode or the brightness fading mode. If the time fading mode is set, the method proceeds to step S80 in which the ADF opens gradually with time, as discussed above in connection with FIG. 4. If the brightness fading mode is set, the method continues to step S160.

In step S160, the ADF opens gradually in accordance with the shade level calculation performed at step S130. Thus, for example, as the brightness of a weld gradually decreases with time, the output of the sensor detection at step S110 changes accordingly, a decreased value of brightness is detected, and a different shade level is calculated at step S130, such that the ADF opens gradually as the brightness decreases.

If the eye protection device is provided with only a brightness fading mode, then steps S150 and S80 are omitted, such that the method proceeds from step S70 (if step S70 is included) to step S160, or directly from step S60 (if step S70 is not included) to step S160. If the eye protection device is provided with only a time fading mode, then steps S150 and S160 are omitted, such that the method proceeds from step S70 (if step S70 is included) to step S80, or directly from step S60 (if step S70 is not included) to step S80.

At step S90, the ADF is in an OFF state (undarkened state), and the method returns to step S10.

FIGS. 6-11 show examples of an ADF shade level over time in an eye protection device, such as the eye protection device 20 or 22 of FIG. 2 or FIG. 3, or in an eye protection method, such as the method of FIG. 4 or the method of FIG. 5. In each example, the ADF 500 starts in an undarkened state (also referred to as an open state), and then is driven to a darkened state (also referred to as a closed state) at time T1, upon detection of welding activity by the welding activity detection circuit 200. This transition from the undarkened state to a darkened state should be as fast as possible, such as about 150 microseconds or less, if possible. A darkened state (either constant or varied) is maintained until time T2, at which welding activity is no longer detected, e.g., at a point in time at which an electric welding arc goes off. (Strictly speaking, there may be an inherent, very small delay between the point at which the welding arc goes off and the point at which welding activity is no longer detected, but for purposes of this application these points will be treated as the same point in time.) Thereafter, the controller 100 controls the ADF driver 400 to open the ADF 500 (i.e., cause the ADF 500 to transition from a darkened state to the undarkened state), as described below.

Figure 6:
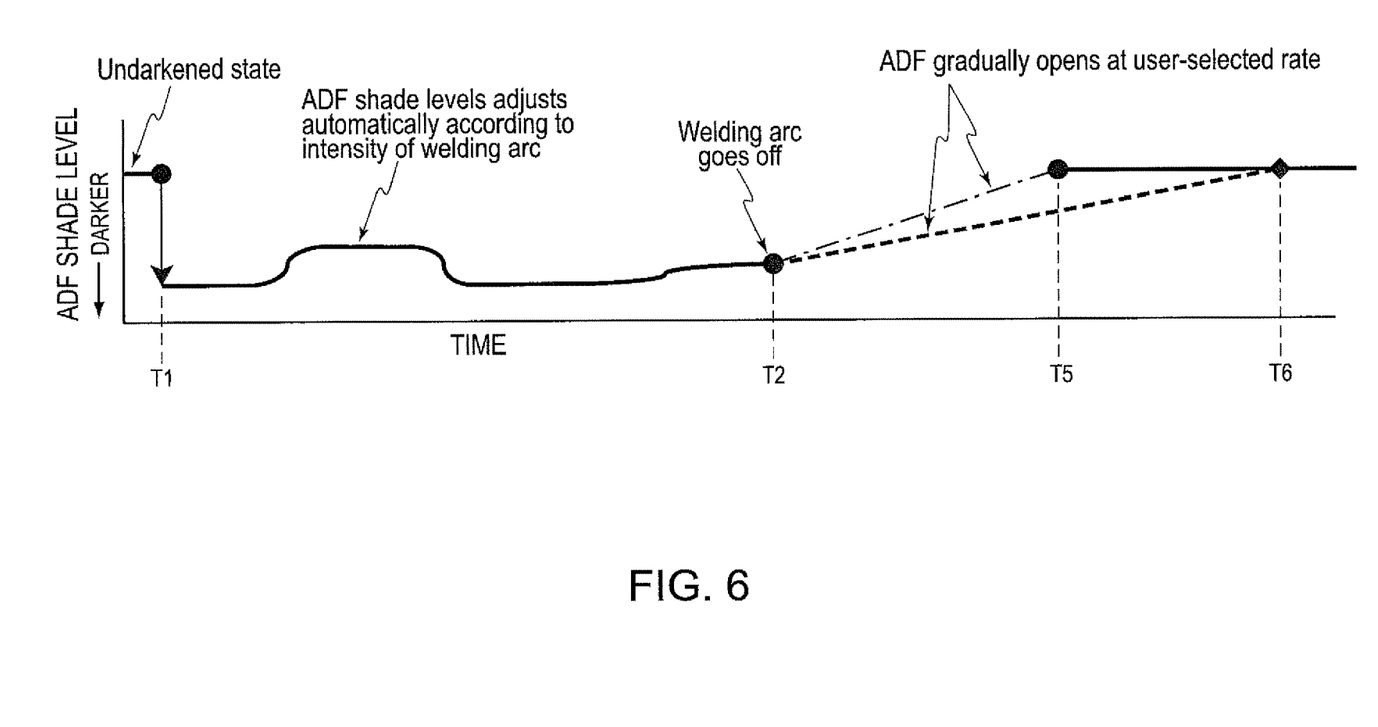
FIG. 6 is a chart showing first and second examples of an ADF shade level over time in an eye protection device.

FIG. 6 shows an example in which the welding arc goes off at time T2, and the ADF 500 is gradually opened at a user-selected gradient, spanning a transition period from either T2 to T5 or from T2 to T6 The sloped lines from T2 to T5 and from T2 to T6 each represent a gradient of change of light transmission values between the darkened state and the undarkened state during the transition period. The user-selected gradient is selected by the user through the user interface 600. The user interface 600 may, for example, be configured to allow the user to select from among a plurality of preset gradients, or to allow the user to input any desired gradient.

Figure 7:
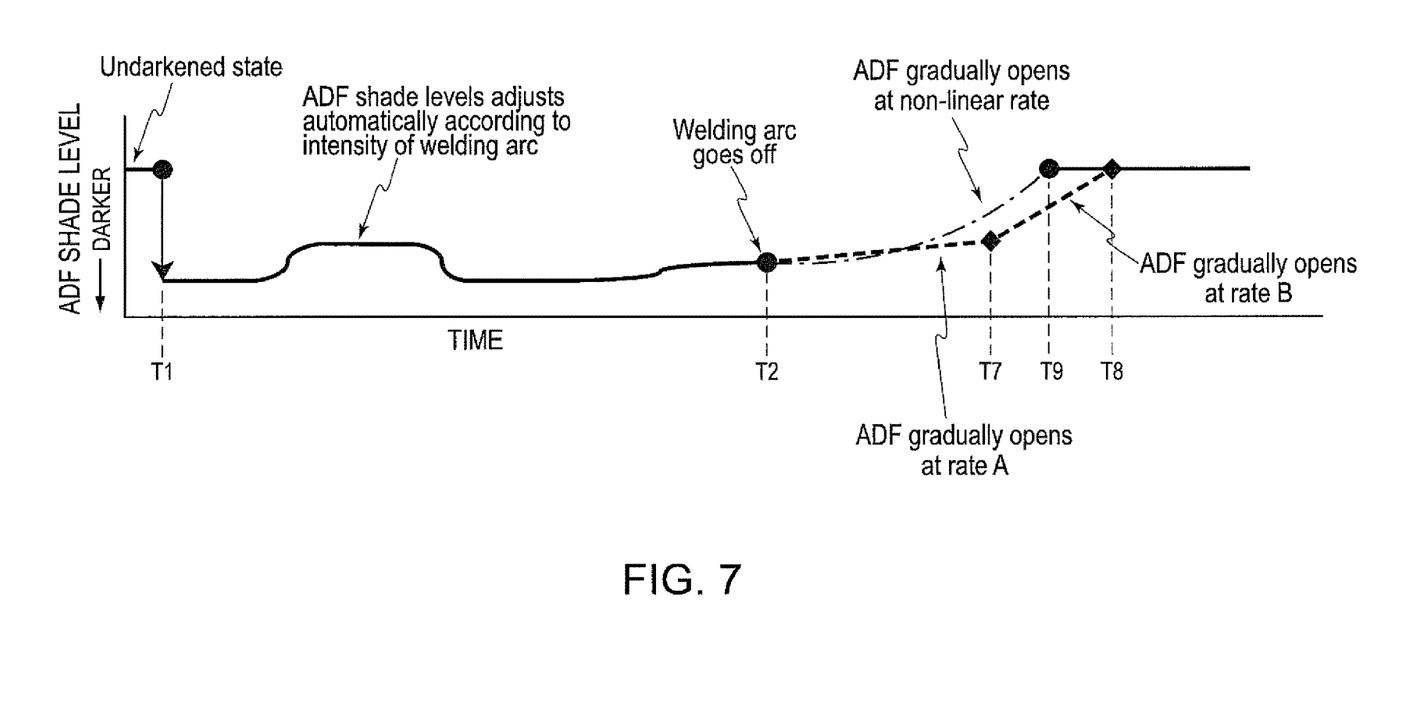
FIG. 7 is a chart showing third and fourth examples of an ADF shade level over time in an eye protection device.

FIG. 7 shows an example in which the welding arc goes off at time T2, and the ADF 500 is gradually opened during user-selected or factory-set transition period from either T2 to T8 or from T2 to T9. The transition period from T2 to T8 includes two separate linear gradients, one from T2 to T7 and one from T7 to T8. The number of separate gradients is not limited to two, and may alternatively be three or more. The transition period from T2l to T9 includes a non-linear gradient. A benefit of having two or more separate linear gradients, and/or a non-linear gradient, is that in an early stage of transition, when the brightness of the weld may decrease relatively slowly, the transition may be set to be more gradual than in a later stage, when the brightness of the weld may decrease relatively quickly. Thus, the transition from the darkened state to the undarkened state may better match the change in weld brightness, as compared to the case of a single linear gradient.

Figure 8:
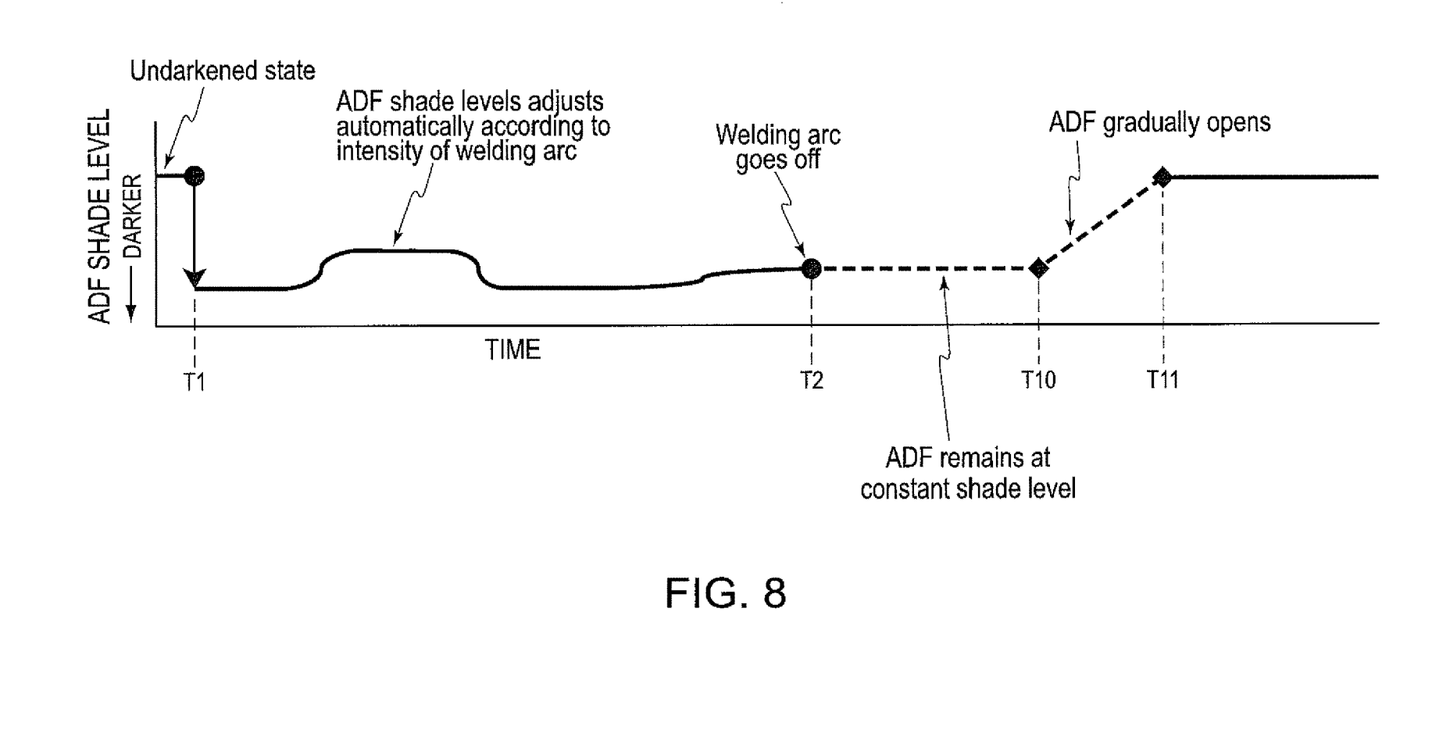
FIG. 8 is a chart showing a fifth example of an ADF shade level over time in an protection device.

FIG. 8 shows an example in which the welding arc goes off at time T2, and the ADF remains at a constant shade level in the period from T2 to T2. The period from T2 to T10 may be either a factory-set period or a user-selected period. Then, in the period from T10 to T11, the ADF gradually opens. The gradient of opening in the period from T10 to T11 may be either a factory-set gradient or a user-selected gradient. In embodiments, the period from T2to T10 may be omitted, and the ADF 500 may immediately begin transitioning from a darkened state to the undarkened state along a factory-set gradient (which may be either linear, or non-linear as shown in FIG. 7), upon cessation (or end of detection) of the welding are at T2.

Figure 9:
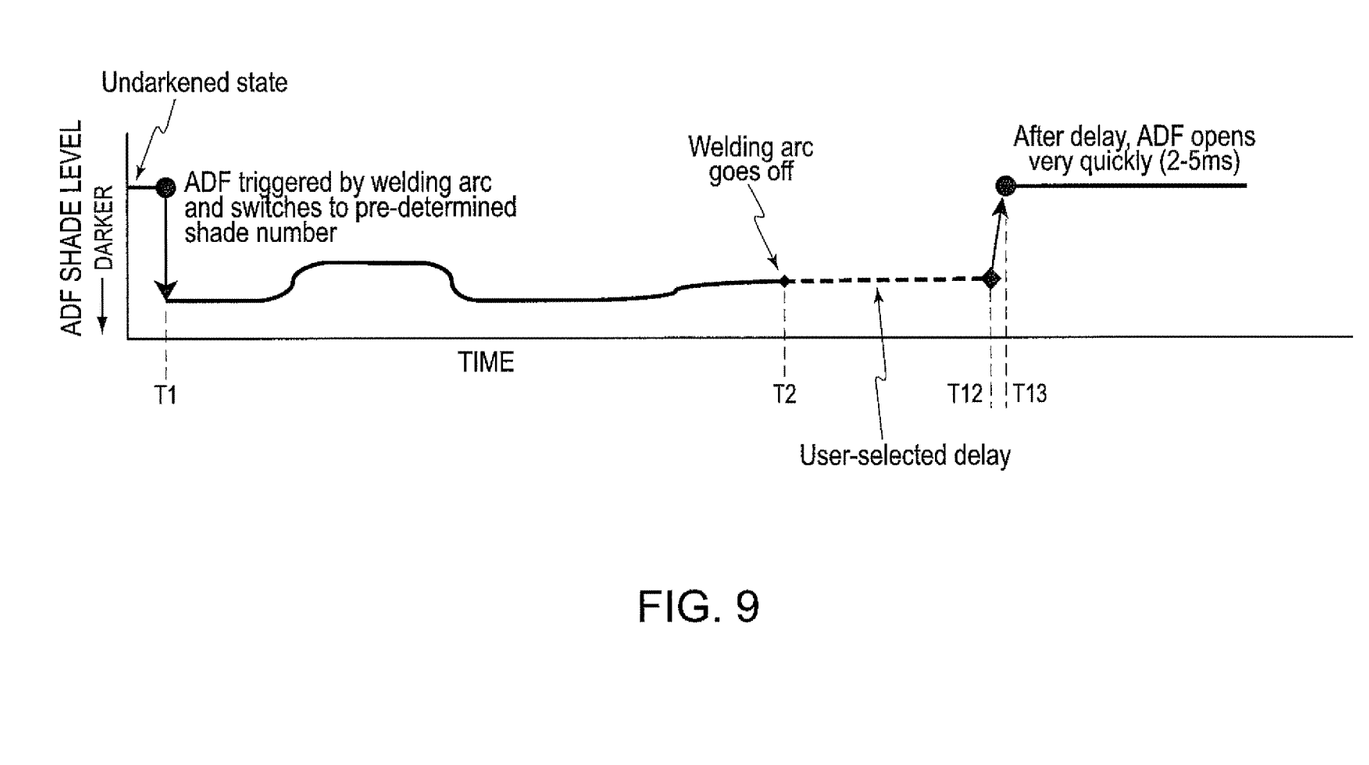
FIG. 9 is a chart showing a sixth example of an ADF shade level over time in an eye protection device.

FIG. 9 shows an example in which the welding arc goes off at time T2, and the ADF remains at a constant shade level in the period from T1 to T12. In this case, the period from T2 to T12 includes at least a user-selected delay. The period from T2to T12 may also include a factory-set delay, to help ensure safety (e.g., to prevent the user from setting a delay that is too short to account for the weld brightness immediately after the end of welding activity). Then, in the period from T12 to T13, the ADF opens very quickly, e.g., in the conventional range of from about 2 milliseconds to about 5 milliseconds.

Figure 10:
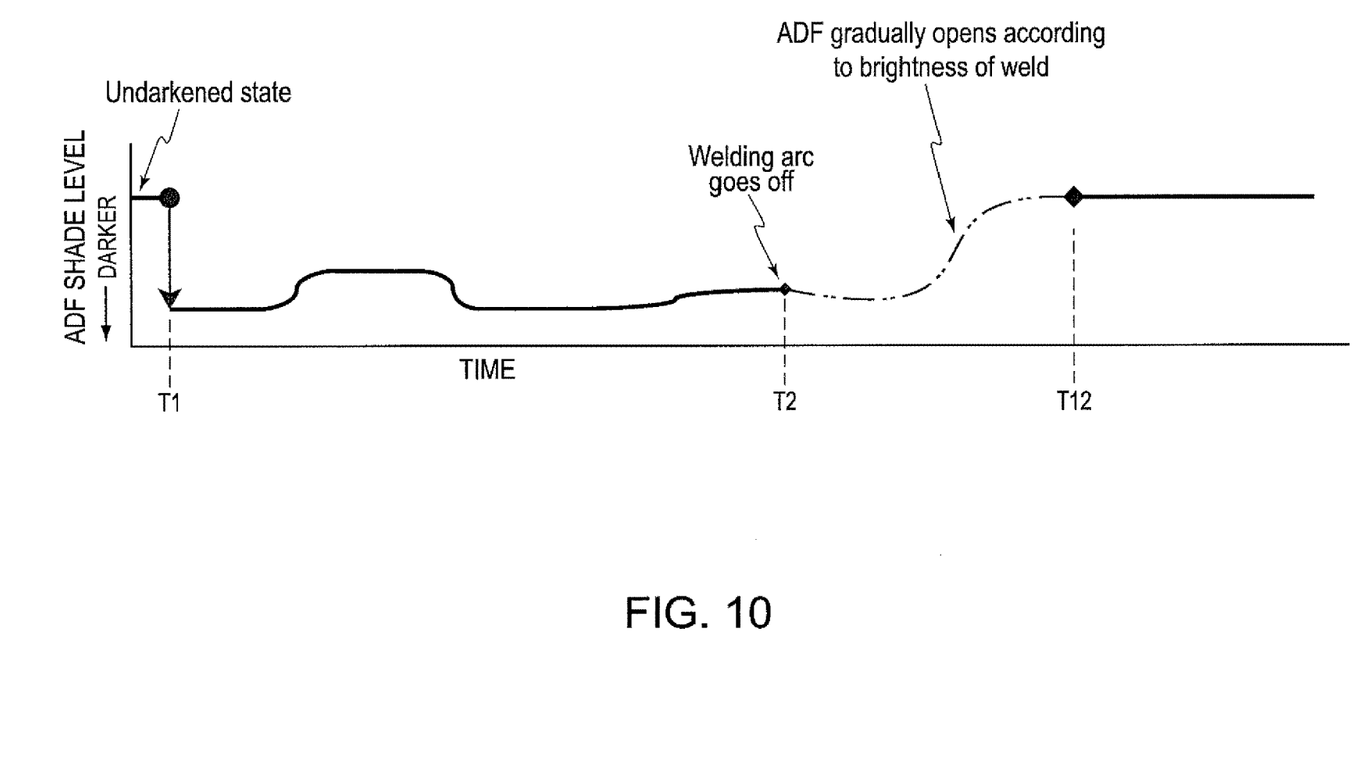
FIG. 10 is a chart showing a seventh example of an ADF shade level over time in an eye protection device.

FIG. 10 shows an example in which, after the welding activity ends at time T2, the ADF shade level changes according to changes in the brightness of the weld, detected, e.g., by the sensor circuit 310 of FIG. 3. The curve from T2 to T12 may follow a series of shade levels that are pre-mapped to respective brightness levels in a lookup table or the like stored in the controller 100. The pre-mapping of shade levels to brightness levels may, for example, be in accordance with the specifications of European Standard EN 379. Alternatively, for example in an analog embodiment, the appropriate shade number of the ADF 500 may be determined by the transmission control circuit 300 comparing the detected brightness level with an illuminance/shade number characteristic curve, such as that set forth in EN 379. The controller 100 receives the result of this comparison and causes a corresponding driving voltage to be applied from the ADF driver 400 to the ADF 500.

Figure 11:
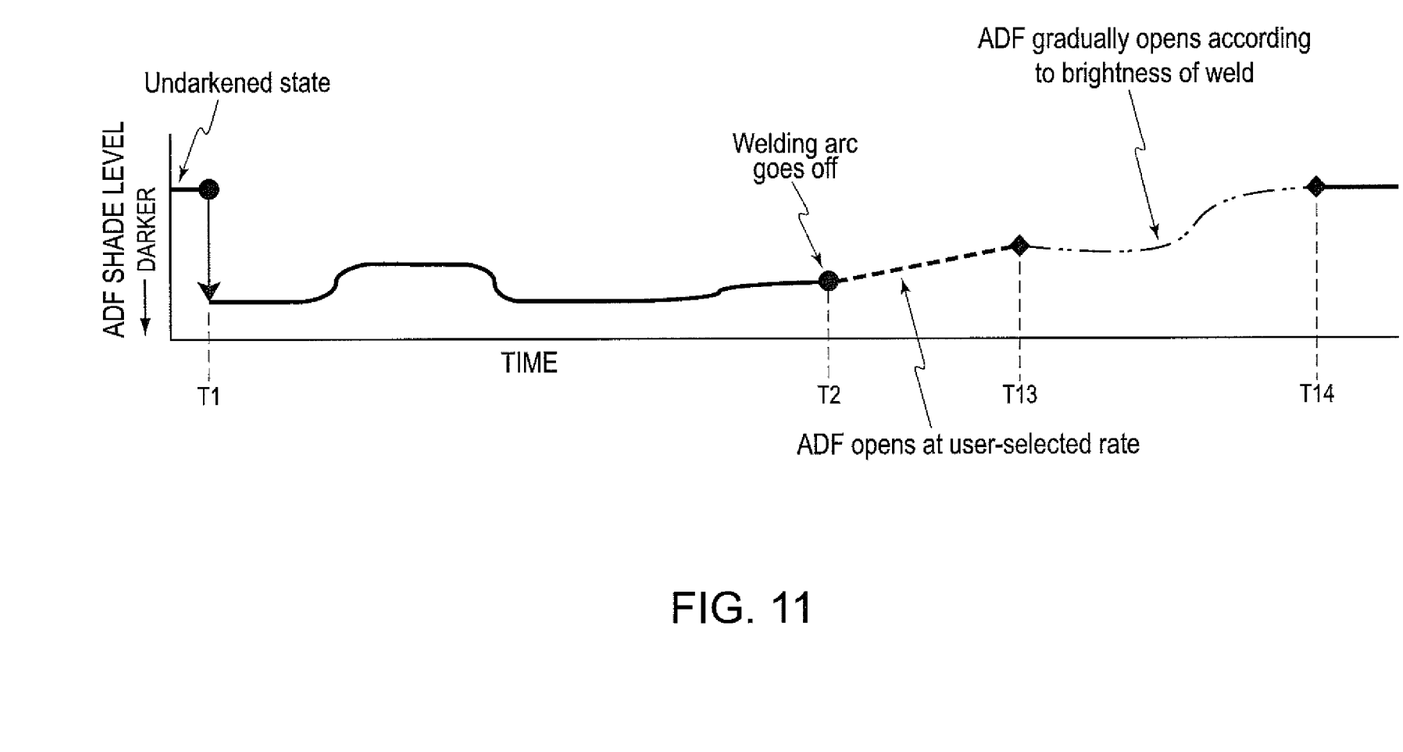
FIG. 11 is a chart showing an eighth example of an ADF shade level over time in an eye protection device.

FIG. 11 shows an example in which, after the welding activity ends at time T2, the ADF shade level changes at a user-selected rate during the period from T2 to T13. Then, during the period from T13 to T14, the shade level changes according to changes in the brightness of the weld (e.g., using pre-mapped values as discussed in connection with FIG. 10).

The transition period in any of FIGS. 6-11 may be at least 10 milliseconds, and may be about 50 milliseconds, about 100 milliseconds, about 150 milliseconds, about 200 milliseconds, about 250 milliseconds, 500 milliseconds, 750 milliseconds, 1000 milliseconds, 1.5 seconds, 2 seconds, 3 seconds, 4 seconds, 5 seconds, and so on. The transition period may be long enough to be perceived by the human eye, rather than being perceived as an instantaneous change. However, in some embodiments, a user may select a gradient such that the transition period is very short, such as from about 1 millisecond to about 5 milliseconds. The user-selected delay in FIG. 9 may be the same as, shorter than, or longer than the conventional delay of from about 200 milliseconds to about 500 milliseconds. The maximum delay, or combination of delays and/or gradients, may be any desired value up to about 5 seconds, although values of more than about 2 seconds might be viewed as less practical from the standpoint of allowing a welder to maintain position of a welding electrode near the weld between welding activities. However, for applications involving high welding amperage and thick metal, in which the weld may continue to glow for up to a minute or longer, the transition to the undarkened state may be set also to take up to about a minute or longer.

Thus, in each of the examples shown in FIGS. 6-11, the ADF driver 400 of FIG. 3 or 4:
(i) controls a transition period from (a) a beginning of transition of the optical filter from the darkened state to the undarkened state (e.g., T2 in FIGS. 6-7 and 10-11, T10 in FIG. 8) to (b) an end of transition of the optical filter from the darkened state to the undarkened state (e.g., T5 or T6 in FIG. 6, T8 or T9 in FIG. 7, T11 in FIG. 8, T14 in FIG. 11) to include a user-selected gradient,
(ii) inserts a user-selected delay between (a) an end of welding activity detection (T2) and (b) the beginning of transition of the optical filter from the darkened state to the undarkened state (T10 in FIG. 8, T12 in FIG. 9),
(iii) causes variation of light transmission values of the optical filter between the darkened state and the undarkened state based on varying brightness detected by a brightness sensor during the transition period; and/or
(iv) controls the transition period to be at least 10 milliseconds. In embodiments, all of (i), (ii), (iii) and (iv) may be available in a single eye protection device, either in a single mode or one or more separate modes. For example, an eye protection device may have only a single mode in which a user-selected delay is inserted after the end of welding activity detection, one or more user-selected gradients are included in a portion of the transition period, light transmission values of the optical filter vary based on brightness detection during another portion of the transition period, and the transition period is at least 10 milliseconds. As another example, various modes including these features separately or in any combination may be made available for user selection.

In the foregoing examples of FIGS. 6-11, the ADF shade level is shown to vary in the period from T1 to T2, which indicates that brightness is being detected during welding and that the shade level is varied in response to changes in brightness. However, embodiments are also possible in which the shade level is held constant during welding.

In the foregoing examples in which a user-selected delay is included, e.g., in the transition period or in the period between the end of welding activity detection (e.g., the point at which welding stops) and the beginning of the transition period, the user interface 600 may, for example, be configured to allow the user to select from among various predefined values by pushing separate microswitches or separate soft switches on an LCD display or the like, or a single microswitch that toggles through selection options on an LCD display, or by turning a knob to a position corresponding to a desired value. Alternatively, the user interface 600 may be configured to allow the user to input any desired value, rather than selecting from among predetermined values.

Figure 12:
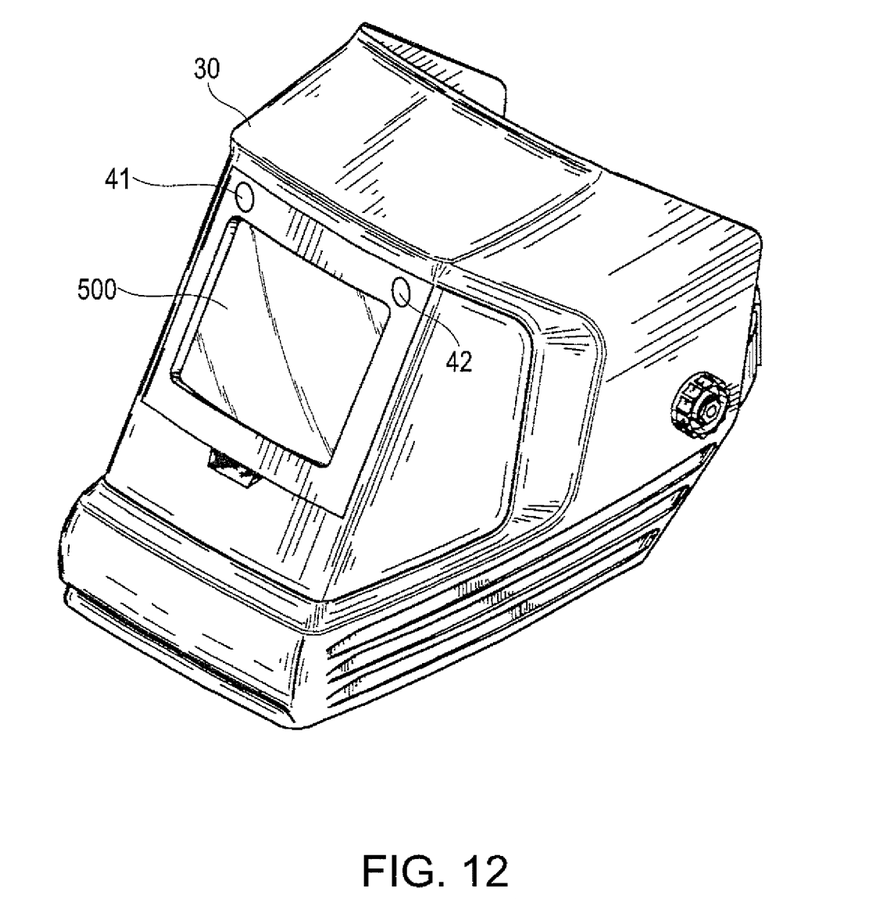
FIG. 12 illustrates an exemplary welding mask.

FIG. 12 illustrates an exemplary welding mask 30, in which the eye protection device 20 or 22 described above is included. The ADF 500 is positioned to shield the eyes of a welder. The welding mask 30 includes sensors 41 and 42, which correspond to the sensors associated with the sensor circuit 210 and/or the sensor circuit 310 described above.

While specific embodiments have been described above, these embodiments should be viewed as illustrative and not limiting. Various changes, substitutes, improvements or the like are possible within the spirit and scope of the invention. For example, various ones of the above-disclosed and other features and functions, or alternatives thereof, may be desirably combined into other embodiments. For example, any number of the above-described options for user-selected delay, pre-set delay, and gradual ADF opening in response to changes in brightness can be made available in a single eye protection device.

As another example, the embodiments described above have been in the context of electric arc welding, but embodiments are also possible in the context of other types of welding that emit bright light, such as gas welding.

What is claimed is:

1. An eye protection method, comprising:
(i) automatically controlling a controllable optical filter via a filter driver of an eye protection device to be in an undarkened state if welding activity is not detected;
(ii) automatically controlling the optical filter via the filter driver of the eye protection device to be in a darkened state if welding activity is detected;
(iii) automatically controlling a transition period via the filter driver of the eye protection device by electrically triggering the optical filter from (a) a beginning of transition of the optical filter from the darkened state to the undarkened state to (b) an end of transition of the optical filter from the darkened state to the undarkened state to include a linear user-selected gradient at which a shade level of the optical filter changes linearly at a user selected rate, wherein the optical filter is gradually opened at the user-selected gradient, spanning a first part at the beginning of the transition period, such that at least one intermediate shade level of the optical filter between the darkened state and the undarkened state is presented during the first part of the transition period, wherein the user-selected gradient is selected by the user through a user interface including one or more microswitches, one or more soft switches on a display, one or more knobs, or any combination of switches and knobs, where the user selects the user-selected gradient from among a plurality of preset gradients;

(iv) during a second part of the transition period, subsequent to the first part, causing variation of the shade level of the optical filter between the darkened state and the undarkened state based on varying brightness detected during the transition period, such that at least one intermediate shade level of the optical filter between the darkened state and the undarkened state is presented during the second part of the transition period, wherein, during the second part, the optical filter shade level changes according to changes in the brightness of the weld, detected by a sensor circuit, wherein the controller causes the driver of the optical filter to drive the optical filter to a shade level based on a perceived brightness level, which results in a course of the shade level following a series of shade levels that are pre-mapped to respective brightness levels in a virtual lookup table stored in a controller; and (v) automatically controlling the transition period via the filter driver of the eye protection device to be at least 10 milliseconds.

2. The method according to claim 1, further comprising inserting a user-selected delay between (a) the end of welding activity detection and (b) the beginning of transition of the optical filter from the darkened state to the undarkened state through the user interface.

3. The method according to claim 1, wherein, while controlling the transition period, the optical filter shade level changes at a user-selected rate during the first part of the transition period and subsequently the shade level changes according to changes in the brightness of the weld using pre-mapped values during the second part of the transition period.

4. The method according to claim 1, wherein the transition period is at least 1000 milliseconds.

5. An eye protection method, comprising:

(i) automatically controlling a controllable optical filter via a filter driver of an eye protection device to be in an undarkened state if welding activity is not detected;

(ii) automatically controlling the optical filter via the filter driver of the eye protection device to be in a darkened state if welding activity is detected;

(iii) automatically controlling a transition period via the filter driver of the eye protection device by electrically triggering the optical filter from (a) a beginning of transition of the optical filter from the darkened state to the undarkened state to (b) an end of transition of the optical filter from the darkened state to the undarkened state to include a linear user-selected gradient at which a shade level of the optical filter changes linearly at a user selected rate, wherein the optical filter is gradually opened at a user-selected gradient, wherein the user-selected gradient is selected by the user through a user interface including one or more microswitches, one or more soft switches on a display, one or more knobs, or any combination of switches and knobs, where the user selects the user-selected gradient from among a plurality of preset gradients; and (iv) automatically controlling the transition period via the filter driver of the eye protection device to be at least 10 milliseconds.

* * * * *